(12) United States Patent
Paul et al.

(10) Patent No.: US 11,499,051 B2
(45) Date of Patent: Nov. 15, 2022

(54) PROCESS FOR EXTRACTION AND ISOLATION OF BIOCHEMICAL CONSTITUENTS FROM ALGAE

(71) Applicant: ALGAVISTA GREENTECH PVT. LTD., Tamil Nadu (IN)

(72) Inventors: Jose Paul, Vazhakkala-Kerala (IN); Sindu Ros, Thrissur-Kerala (IN)

(73) Assignee: ALGAVISTA GREENTECH PVT. LTD., Chennai (IN)

( * ) Notice: Subject to any disclaimer, the term of this patent is extended or adjusted under 35 U.S.C. 154(b) by 883 days.

(21) Appl. No.: 16/353,379

(22) Filed: Mar. 14, 2019

(65) Prior Publication Data
US 2019/0352509 A1    Nov. 21, 2019

(30) Foreign Application Priority Data
May 15, 2018   (IN) .............................. 201841018141

(51) Int. Cl.
| | | |
|---|---|---|
| *C09B 61/00* | (2006.01) | |
| *B01D 3/14* | (2006.01) | |
| *B01D 11/02* | (2006.01) | |
| *B01D 21/26* | (2006.01) | |
| *B01D 61/14* | (2006.01) | |

(52) U.S. Cl.
CPC .............. *C09B 61/00* (2013.01); *B01D 3/145* (2013.01); *B01D 11/0288* (2013.01); *B01D 11/0292* (2013.01); *B01D 21/262* (2013.01); *B01D 61/145* (2013.01); *B01D 61/146* (2022.08); *B01D 2311/04* (2013.01); *B01D 2311/06* (2013.01); *B01D 2311/2669* (2013.01); *B01D 2311/2673* (2013.01); *B01D 2311/2676* (2013.01)

(58) Field of Classification Search
CPC ..... C09B 61/00; B01D 3/145; B01D 11/0288; B01D 11/0292; B01D 21/262; B01D 61/142; B01D 61/145; B01D 2311/04; B01D 2311/06; B01D 2311/2669; B01D 2311/2673; B01D 2311/2676; B01D 3/146; B01D 11/02; B01D 11/0207; B01D 21/26; B01D 37/00; B01D 61/16; B01D 61/20; B01D 2311/2649; A23J 1/009; A23J 3/20; A23L 5/43; A23L 33/195; C12N 1/066; C07K 14/795; C07K 1/34; C07K 1/145; C07K 14/405; C07K 1/14; C07K 1/36; C12P 7/64; C12P 23/00; C11B 1/10; C11B 1/108; C11B 1/04; C11B 1/12; C11B 3/00; C11B 3/001; C11B 3/006; C11B 3/02; C11B 3/04; C11B 11/02; C11B 11/0203; B01J 43/00; B01J 39/20; B01J 41/14; C02F 1/26; C02F 2103/22; C02F 2103/36; A23K 1/14; A23K 1/288; A23K 10/16; A23K 10/18; A23K 10/20; A23K 10/22; A23K 10/30; A23K 50/80; C10L 1/02; C10L 1/10; C10L 1/026; C10L 1/1802; C10L 8/00; C10L 5/42; C10L 2200/0469; C10L 2200/0474; C10L 2200/0476; C10L 2200/0484; Y02E 50/10; Y02E 50/13; Y02E 10/34; C11C 3/00; C11C 3/02; C11C 3/003; A01K 61/00; A01K 61/02; A01K 61/007; A01K 61/008; A01K 63/00
USPC .............. 119/213, 215, 226; 405/52, 75, 80; 210/167.21, 170.02, 170.11, 257.1, 511, 210/634; 44/307, 385, 605; 47/1.4, 60, 47/62, 62 r, 62 a; 554/8, 174, 175; 530/370, 412, 422
See application file for complete search history.

(56) References Cited

U.S. PATENT DOCUMENTS

| | | | | |
|---|---|---|---|---|
| 4,162,946 | A * | 7/1979 | Thelen .................... | B01D 3/146 203/91 |
| 4,851,339 | A * | 7/1989 | Hills ....................... | C12P 23/00 435/946 |
| 2004/0262221 | A1* | 12/2004 | Herold ............... | B01D 11/0288 210/639 |
| 2013/0122180 | A1* | 5/2013 | Brooks ................ | A23D 7/0056 426/609 |
| 2014/0318000 | A1* | 10/2014 | Goetheer ................. | C12N 1/12 435/257.1 |
| 2017/0267715 | A1* | 9/2017 | Fernando ............... | C07K 1/145 |
| 2018/0305656 | A1* | 10/2018 | Wendt ..................... | C12N 1/04 |
| 2019/0142880 | A1* | 5/2019 | Scoglio ................ | A61K 9/0034 424/93.4 |

FOREIGN PATENT DOCUMENTS

| | | |
|---|---|---|
| CN | 101607988 A | 12/2009 |
| EP | 2735232 A1 | 5/2014 |

OTHER PUBLICATIONS

Shaochen Guan, "Extracting phycocyanin from spirulin and hydrothermal liquefaction of its residues to produce bio-crude oil", Thesis published at the Graduate School of the University of Illinois at Urbana-Champaign, 2016. (Year: 2016).*

(Continued)

*Primary Examiner* — Joseph W Drodge

(57) ABSTRACT

The present disclosure is in the field of 'pharmacognosy' and 'chemistry of natural products'. The present disclosure generally relates to a process of isolation and purification of Biochemical Constituents from algae. The present disclosure particularly relates to a process of isolation and purification of Biochemical Constituents from a biomass of cyanobacteria. The present disclosure provides a process for isolating and extracting phycocyanins, chlorophylls, proteins and polysaccharides from the spirulina biomass.

16 Claims, No Drawings

(56) References Cited

OTHER PUBLICATIONS

Written Opinion of the International Searching Authority and International Search Report for PCT Application No. PCT/IB2019/052004 dated Jun. 13, 2019.
Parimi et al., "Optimization of protein extraction from Spirulina platensis to generate a potential co-product and a biofuel feedstock with reduced nitrogen content", Frontiers in Energy Research, vol. 3, Jun. 23, 2015, p. 1-9.
Kumar et al., "Extraction and purification of C-phycocyanin from Spirulina platensis (CCC540)", Indian Journal of Plant Physiology, vol. 19, No. 2, Jun. 1, 2014, p. 184-188.
Moraes et al., "C-phycocyanin extraction from Spirulina platensis wet biomass", Brazilian Journal of Chemical Engineering, vol. 28, No. 1, Mar. 1, 2011, p. 45-49.
Sivasankari et al., "Comparison of Different Extraction methods for Phycocyanin Extraction and Yield from Spirulina platensis", Int.J. Curr.Microbiol.App.Sci,vol. 3, Jan. 1, 2014, p. 904-909.
Hosikian et al., "Chlorophyll Extraction from Microalgae: A Review on the Process Engineering Aspects", International Journal of Chemical Engineering, vol. 2010, Jan. 1, 2010, p. 1-11.

\* cited by examiner

PROCESS FOR EXTRACTION AND ISOLATION OF BIOCHEMICAL CONSTITUENTS FROM ALGAE

CROSS REFERENCE TO RELATED APPLICATION

This application claims priority to and benefit of Indian Patent Application No. 201841018141, filed May 15, 2018, the disclosure of which is hereby incorporated herein by reference in its entirety.

FIELD OF THE INVENTION

The present disclosure is in the field of 'pharmacognosy' and 'chemistry of natural products'. The present disclosure generally relates to a process of isolation and purification of Biochemical Constituents from algae. The present disclosure particularly relates to a process of isolation and purification of Biochemical Constituents from a biomass of cyanobacteria. The present disclosure provides a process for isolating and extracting phycocyanins, chlorophylls, proteins and polysaccharides from the spirulina biomass.

BACKGROUND OF THE INVENTION

Several algae species have gained significant importance because of their utility in therapeutic applications and their use in food supplements due to their valuable biochemical constituents particularly proteins, minerals, chlorophyll and vitamins.

Cyanobacteria (Spirulina algae) contain phycocyanin (blue), allophycocyanin (blue-grey) and phycoerythrin (red) pigments. These pigments are protein molecules and called Phycobiliproteins can be used as natural pigments in the food, drug and cosmetic industries to replace the currently used synthetic pigments.

Phycobiliproteins are homologous, intensively coloured protein pigments functioning as photosynthetic light-harvesting complexes. Their ability to absorb light in the visible spectrum is due to various chromophore prosthetic groups, which are linear tetrapyrroles covalently attached to apoprotein. The chromophore composition influences spectral properties and serves as one of the main characteristics of these pigments.

Spirulina contains approximately 12-20% phycocyanin which is one of the commercially promising blue biopigment. Phycocyanin is a water soluble phycobili-protein that occurs in two forms called $\alpha$ and $\beta$ phycobilin, a tetrapyrrole chromophore. It also contains other phycobiliproteins mainly allophycocyanin and together it forms a supramolecular complex called phycobilisomes.

These prosthetic groups account for about 4% of the algae mass, indicating the presence of about sixteen chromophoric groups per unit molecular weight. It occurs in four different structural forms, monomeric, trimeric, hexameric and decameric, and is the most abundant pigment in blue-green algae, accounting for more than 20% of algal dry weight.

The Cyanobacterium Spirulina possess a wide range of biochemical constituents such as phycobiliproteins, colored components, polysaccharides and several other proteins. The principal phycobiliproteins of Cyanobacterium Spirulina are phycocyanin, allo-phycocyanin and phycoerythrin. The phycocyanin is a blue colored pigment which has numerous application in health and food supplements.

The process disclosed in the prior art have several disadvantages with regards to the extraction efficiency, removal of suspended particles from water phase by centrifugation, very low filtration rates, usage of flocculants like calcium phosphate, chitosan etc. to remove impurities during centrifugation/filtration making the processes lengthy and cumbersome. Further, the methods disclosed in the prior art are not efficient to get good recovery of phycocyanin. Isolation of phycocyanin water extract from the biomass using filtration technics are not efficient and the prior art processes were not able to completely separate the biomass from the phycocyanin. Accordingly, the isolated phycocyanin have less purity due to the process inefficiency. The water extract of phycocyanin having very high microbiology count also creates process unviable. The challenges in filtration, centrifugation, sterilization and purification made the prior art process unviable in commercial scale production. Further, the extraction methods disclosed in the prior art do not consider freshly harvested and wet biomass as a source in the initial step of extraction procedure, which eventually reduces the yield and makes the separation process challenging to remove the impurities from the final product obtained from the biomass of spirulina.

Accordingly, there is a need for an improved and economically feasible process for the extraction phycocyanin, chlorophyll and proteins from spirulina biomass with good yield and high purity. The present disclosure aims at overcoming the drawbacks of prior art to provide an improved and energy efficient process for the extraction of phycocyanin, chlorophyll and proteins from the freshly harvested and wet biomass of spirulina with good yield and high purity.

SUMMARY OF THE INVENTION

The present disclosure relates to process for extraction and isolation of biochemical constituents selected from a group comprising phycocyanin, magnesium chlorophyll, hydrolysed protein and combinations thereof from wet algal biomass comprising steps of:

cooling the aqueous solution of algal biomass;

pressure homogenizing the wet algal biomass and extraction of the biomass with salt solution in presence of acidic conditions to obtain a suspension;

subjecting the suspension to a separation process to separate filtrate and residue; and concentrating the filtrate followed by washing with solvent to remove impurities and to obtain purified phycocyanin from the wet algal biomass, or, drying the residue, treating the residue with solvent followed by employing a separation process to obtain a filtrate and a residue-V, and subjecting the filtrate to separation process to obtain purified magnesium chlorophyll from the wet algal biomass, wherein the solvent treatment followed by the separation process is repeated one or more times to obtain multiple filtrates which is combined when subjecting to the separation process;

or drying the residue, treating the residue with solvent followed by employing a separation process to obtain a filtrate and a residue-V, and subjecting the filtrate to separation process to obtain purified magnesium chlorophyll from the wet algal biomass, wherein the solvent treatment followed by the separation process is repeated one or more times to obtain multiple filtrates which is combined when subjecting to the separation process; and mixing residue-V obtained after chlorophyll extraction with water and hydrochloric acid, heating the resulting mixture followed by cooling and adjusting the pH to 5.2 using alkali, filtering the resulting solution to remove residue and to obtain a filtrate, by removing the salt through ultrafiltration, concentrating and spray drying the protein solution to give the hydrolysed protein.

The present disclosure further relates to a process for extraction and isolation of phycocyanin from the wet algal biomass comprises steps of:
    cooling the aqueous solution of algal biomass;
    pressure homogenizing the wet algal biomass and extraction of the biomass with salt solution in presence of acidic conditions under cooling conditions to obtain a suspension, followed by centrifuging the suspension to separate filtrate and residue; and
    concentrating the filtrate followed by washing with solvent to remove impurities and to obtain purified phycocyanin from the wet algal biomass.

The present disclosure relates to a process for extraction and isolation of magnesium chlorophyll from the wet algal biomass comprises steps of:
    cooling the aqueous solution of algal biomass;
    pressure homogenizing the wet biomass and extraction of the biomass with salt solution in presence of acidic conditions under cooling conditions to obtain a suspension, followed by centrifuging the suspension to separate filtrate and residue; and
    drying the residue, treating the residue with solvent followed by filtration to obtain a filtrate and residue-V, and subjecting the filtrate to distillation to obtain the purified magnesium chlorophyll from the wet algal biomass, wherein the solvent treatment followed by filtration is repeated one or more times to obtain multiple filtrates which is combined when subjecting to the distillation.

The present disclosure relates to a process for extraction and isolation of hydrolysed protein from the wet algal biomass comprises steps of:
    cooling the aqueous solution of algal biomass;
    pressure homogenizing the wet biomass and extraction of the biomass with salt solution in presence of acidic conditions under cooling conditions to obtain a suspension, followed by centrifuging the suspension to separate filtrate and residue;
    drying the residue, treating the residue with solvent followed by filtration to obtain a filtrate and residue-V, and subjecting the filtrate to distillation to obtain the purified magnesium chlorophyll from the wet algal biomass, wherein the solvent treatment followed by filtration is repeated one or more times to obtain multiple filtrates which is combined when subjecting to the distillation; and
    mixing residue-V obtained after chlorophyll extraction with water and hydrochloric acid, heating the resulting mixture followed by cooling and adjusting the pH to 5.2 using caustic soda solution, filtering the resulting solution to remove residue and to obtain a filtrate, by removing the salt, concentrating and spray drying the filtrate to give the hydrolysed protein.

DETAILED DESCRIPTION

The freshly harvested cyanobacteria from the open pond was passed through series of filters to separate the algae and it was then washed with several times water and concentrated using decanter centrifuge to 10-20% solid content. The wet biomass contains crude phycocyanin content between 12 and 20.

The present disclosure relates to a process for extraction and isolation of biochemical constituents selected from a group comprising phycocyanin, magnesium chlorophyll, hydrolysed protein and combinations thereof from wet algal biomass comprising steps of:
    cooling the aqueous solution of algal biomass;
    pressure homogenizing the wet algal biomass and extraction of the biomass with salt solution in presence of acidic conditions to obtain a suspension;
    subjecting the suspension to a separation process to separate filtrate and residue; and concentrating the filtrate followed by washing with solvent to remove impurities and to obtain purified phycocyanin from the wet algal biomass,
    or,
    drying the residue, treating the residue with solvent followed by employing a separation process to obtain a filtrate and a residue-V, and subjecting the filtrate to separation process to obtain purified magnesium chlorophyll from the wet algal biomass, wherein the solvent treatment followed by the separation process is repeated one or more times to obtain multiple filtrates which is combined when subjecting to the separation process;
    or
    drying the residue, treating the residue with solvent followed by employing a separation process to obtain a filtrate and a residue-V, and subjecting the filtrate to separation process to obtain purified magnesium chlorophyll from the wet algal biomass, wherein the solvent treatment followed by the separation process is repeated one or more times to obtain multiple filtrates which is combined when subjecting to the separation process; and
    mixing residue-V obtained after chlorophyll extraction with water and hydrochloric acid, heating the resulting mixture followed by cooling and adjusting the pH to 5.2 using alkali, filtering the resulting solution to remove residue and to obtain a filtrate, by removing the salt through ultrafiltration, concentrating and spray drying the protein solution to give the hydrolysed protein.

In an embodiment of the present disclosure, the wet algal biomass is blue-green algae, more preferably spirulina.

In another embodiment of the present disclosure, the blue-green algae is spirulina.

In yet another embodiment of the present disclosure, the solid content of wet spirulina biomass is about 14-20%.

In still another embodiment of the present disclosure, the cooling is carried out at a temperature ranging from about 10° C. to about 30° C., preferably 15° C. to about 20° C.

The present disclosure further relates to a process for extraction and isolation of phycocyanin from the wet algal biomass comprises steps of:
    cooling the aqueous solution of algal biomass;
    pressure homogenizing the wet algal biomass and extraction of the biomass with salt solution in presence of acidic conditions under cooling conditions to obtain a suspension, followed by centrifuging the suspension to separate filtrate and residue; and
    concentrating the filtrate followed by washing with solvent to remove impurities and to obtain purified phycocyanin from the wet algal biomass.

In an embodiment of the present disclosure, the process wherein said process for extraction and isolation of phycocyanin from wet spirulina biomass comprising steps of:
A. cooling the solution of biomass under stirring conditions;
B. pressure homogenizing the biomass obtained from previous step to obtain the homogenized biomass;
C. mixing the salt solution with the homogenized biomass to obtain a mixture I;
D. adjusting the pH of the mixture I with acid(s) to obtain acid treated mixture;
E. cooling the acid treated mixture followed by stirring to obtain the cooled acid treated mixture;
F. separating the suspended solids from the cooled acid treated mixture to obtain filtrate-I and residue I;
G. subjecting the filtrate-I obtained from step (F) through ultrafiltration to obtain the concentrated liquid;
H. washing the concentrated liquid obtained from the step (G) with water to obtain a solution containing the biochemical constituent(s) along with impurities;
I. subjecting the solution obtained from step (H) through ultrafiltration repeatedly to obtain further concentrated solution;
J. mixing the concentrated solution obtained from step (I) with filtering agent/filter aid followed by centrifugation to obtain the filtrate-II which is cooled;
K. mixing the solvent with filtrate-II obtained from step (J) to obtain a mixture-II and filtering the mixture-II by fine filtration through fine membrane filter followed by ultrafiltration to obtain filtrate III;
L. mixing the solvent with filtrate III obtained from step (K) to obtain a mixture-IV and filtering the mixture-IV through ultrafiltration to obtain concentrated filtrate-IV; and
M. mixing the concentrated filtrate-IV with a sugar, followed by filtration and spray drying to obtain the phycocyanin.

In an embodiment of the present disclosure, the process for extraction and isolation of phycocyanin from wet spirulina biomass further comprises the step of purification of residue-I in step F, wherein about 3 to 5 times of water is mixed with residue-I and subjected to ultrafiltration to obtain the residual filtrate, wherein said residual filtrate is added to filtrate I.

In another embodiment of the present disclosure, the process for extraction and isolation of phycocyanin from wet spirulina biomass is carried out at a pH ranging from about 4 to 6 and at a temperature ranging from about 10° C. to 25° C.

In yet another embodiment of the present disclosure, the process of centrifugation in the process for extraction and isolation of phycocyanin is carried out at a speed of about 6000 rpm to 8000 rpm.

In still another embodiment of the present disclosure, the process of ultrafiltration in the process for extraction and isolation of phycocyanin is carried out using a 10-100 KDa membrane.

In still another embodiment of the present disclosure, the process of stirring/mixing is carried out by a stirrer or a mixer.

In still another embodiment of the present disclosure, the biomass is homogenized by a homogenizer.

In still another embodiment of the present disclosure, the homogenization is carried out under pressure.

In still another embodiment of the present disclosure, the biomass is homogenized by a pressure homogenizer.

In still another embodiment of the present disclosure, the homogenization is carried out under 100-300 bar pressure.

In still another embodiment of the present disclosure, the process of pressure homogenization in the process for extraction and isolation of phycocyanin is carried out by a pressure homogenizer.

In still another embodiment of the present disclosure, the process of filtration in the process for extraction and isolation of phycocyanin is carried out by filter(s).

In still another embodiment of the present disclosure, the salt solution is sodium chloride solution, calcium chloride solution or a combination of sodium chloride solution and calcium chloride solution.

In still another embodiment of the present disclosure, the concentration of the salt solution ranges from about 5% to 10%.

In still another embodiment of the present disclosure, the concentration of the salt solution ranges from 3 to 6%.

In still another embodiment of the present disclosure, the concentration of the salt solution is 8%.

In still another embodiment of the present disclosure, the concentration of the salt solution is 4%.

In a preferred embodiment of the present disclosure, the concentration of the calcium chloride solution is 4%.

In a preferred embodiment of the present disclosure, the concentration of the calcium chloride solution is 8%.

In a preferred embodiment of the present disclosure, the concentration of the sodium chloride solution is 8%.

In still another embodiment of the present disclosure, the mixture I comprises salt solution and homogenized biomass.

In still another embodiment of the present disclosure, the concentration of the salt solution in mixture I ranges from 1-4%.

In still another embodiment of the present disclosure, the concentration of the salt solution in mixture I ranges from 2-3%.

In a preferred embodiment of the present disclosure, the concentration of the calcium chloride solution in mixture I ranges from 2-3%.

In another preferred embodiment of the present disclosure, the concentration of the sodium chloride solution in mixture I ranges from 2-3%.

In still another embodiment of the present disclosure, the solvent is selected from a group comprising water, organic solvent, inorganic solvent and combinations thereof.

In still another embodiment of the present disclosure, the acid is selected from a group comprising hydrochloric acid, citric acid, tartaric acid, ascorbic acid and combinations thereof.

In still another embodiment of the present disclosure, the concentration of the acid solution ranges from about 0.5% to 5%.

In a preferred embodiment of the present disclosure, the concentration of the acid solution ranges from 0.75% to 2.5%.

In a more preferred embodiment of the present disclosure, the concentration of the acid solution is 1%.

In still another embodiment of the present disclosure, the mixture I comprises salt solution and homogenized biomass.

In still another embodiment of the present disclosure, the pH of the mixture I is adjusted by adding acid.

In still another embodiment of the present disclosure, the pH of the mixture I is adjusted to a range from 4 to 6 by adding acid.

In a preferred embodiment of the present disclosure, the pH of the mixture I is adjusted to 5 by adding acid.

In still another embodiment of the present disclosure, the acid treated mixture comprises acid and the mixture I.

In a preferred embodiment of the present disclosure, the acid treated mixture comprises citric acid and the mixture I.

In still another embodiment of the present disclosure, the filtrate I is a filtrate which is devoid of insoluble solids obtained from the filtration of acid treated mixture.

In a preferred embodiment of the present disclosure, the filtrate I is a filtrate which is devoid of insoluble solids obtained from the filtration of citric acid treated mixture.

In still another embodiment of the present disclosure, the filtration is carried out by filter(s).

In still another embodiment of the present disclosure, the filter is selected from a group comprising centrifuge or clarifier.

In still another embodiment of the present disclosure, the filtrate I is subjected to further filtration to concentrate the filtrate I to obtain a concentrated liquid.

In still another embodiment of the present disclosure, the concentrated liquid is concentrated form of filtrate I.

In still another embodiment of the present disclosure, the biochemical constituent(s) are selected from a group comprising Phycocyanin, Chlorophyll, Polysaccharides, water soluble proteins and combinations thereof.

In still another embodiment of the present disclosure, the mixer is selected from a group comprising mechanical stirrer, anchor, propeller and combinations thereof.

In still another embodiment of the present disclosure, the filter is a centrifuge or a clarifier.

In still another embodiment of the present disclosure, the fine filtration is carried out using 0.01 to 2.0 micron filters.

In still another embodiment of the present disclosure, the suitable filtration is ultrafiltration and/or microfiltration.

The residue part is rich in polysaccharides and water dispersible proteins. The acid hydrolysis of the residue yields water soluble proteins.

In still another embodiment of the present disclosure, 10-100 KDa membrane is used for carrying out ultrafiltration.

In a preferred embodiment of the present disclosure, 20-80 KDa membrane is used for carrying out ultrafiltration.

In still another embodiment of the present disclosure, the filtering agent/filter aid filtration is Celite HYFLO SUPER-CEL.

In still another embodiment of the present disclosure, the solvent is selected from a group comprising water, organic solvents, inorganic solvents or combination thereof.

In still another embodiment of the present disclosure, the sugar is selected from a group comprising trehalose, maltodextrin, ensorbate and combinations thereof.

In still another embodiment of the present disclosure, the phycocyanin content of before spray drying is about 20-25%.

In an embodiment of the present disclosure, the process for extraction and isolation of phycocyanin from wet spirulina biomass comprising steps of:
A. cooling the aqueous solution of spirulina biomass to about 15-20° C. under stirring conditions, wherein said aqueous solution of spirulina biomass is prepared by adding spirulina biomass suspended in demineralised water and cooled to about 15-20° C. under stirring conditions;
B. pressure homogenizing the biomass obtained from previous step at about 100 bar for about 1 hour to obtain homogenized biomass;
C. mixing calcium chloride solution with the homogenized biomass to obtain a mixture I;
D. adjusting pH of the mixture I with citric acid to obtain acid treated mixture maintaining the pH ranging from 4 to 6;
E. cooling the acid treated mixture to about 15-20° C. followed by stirring to obtain the cooled acid treated mixture;
F. separating the insoluble solids from the cooled acid treated mixture to obtain filtrate-I and residue-I by centrifugation at about 7000 rpm;
G. subjecting the filtrate-I through ultrafiltration with a membrane of about 30-50 KD to obtain concentrated liquid;
H. washing the concentrated liquid obtained in step (G) with water to obtain a solution containing the biochemical constituent(s) along with impurities;
I. subjecting the solution obtained in step (H) through ultrafiltration repeatedly to obtain 2% concentrated solution;
J. mixing the concentrated solution obtained in step (I) with Celite HYFLO SUPER-CEL followed by centrifugation at about 6000 rpm to obtain filtrate-II which is cooled;
K. The filtrate-II obtained in step (J) is filtered through 0.1 micron filter at less than 1 bar pressure followed by ultrafiltration to obtain about 8-10% concentrated filtrate-III; and
L. mixing the concentrated filtrate-III with a sugar, followed by filtration and spray drying to obtain the phycocyanin.

In an embodiment of the present disclosure, the phycocyanin content of wet spirulina biomass is about 12-22%.

In another embodiment of the present disclosure, the colour value (10% $E_{618}^{nm}$) of phycocyanin obtained from the above process is 180-200.

In yet another embodiment of the present disclosure, the yield of phycocyanin obtained from the above process is 15-20%.

In still another embodiment of the present disclosure, the crude phycocyanin content of the spirulina extract before spray drying was 40-50%.

In still another embodiment of the present disclosure, the purity of phycocyanin content obtained from the above process is 20-25%.

In an embodiment of the present disclosure, the aqueous suspension of spirulina biomass is prepared by adding spirulina biomass 2000 gms suspended in 2000 ml of demineralized water and cooled to 15-20° C. under stirring using a mechanical stirrer.

The present disclosure furthermore relates to the process for extraction and isolation of magnesium chlorophyll from the wet algal biomass comprises steps of:
 cooling the aqueous solution of algal biomass;
 pressure homogenizing the wet biomass and extraction of the biomass with salt solution in presence of acidic conditions under cooling conditions to obtain a suspension, followed by centrifuging the suspension to separate filtrate and residue; and
 drying the residue, treating the residue with solvent followed by filtration to obtain a filtrate and residue-V, and subjecting the filtrate to distillation to obtain the purified magnesium chlorophyll from the wet algal biomass, wherein the solvent treatment followed by filtration is repeated one or more times to obtain multiple filtrates which is combined when subjecting to the distillation.

In an embodiment of the present disclosure, the wet algal biomass is blue-green algae, more preferably spirulina.

In another embodiment of the present disclosure, the blue-green algae is spirulina.

In yet another embodiment of the present disclosure, the solid content of wet spirulina biomass is about 14-20%.

In still another embodiment of the present disclosure, the cooling is carried out at a temperature ranging from about 10° C. to about 30° C., preferably 15° C. to about 20° C.

In still another embodiment of the present disclosure, the process for extraction and isolation of magnesium chlorophyll from wet spirulina biomass is carried out at a pH ranging from about 3 to 6 and at a temperature ranging from about 10° C. to 25° C.

In still another embodiment of the present disclosure, the process of centrifugation in the process for extraction and isolation of magnesium chlorophyll is carried out at a speed of about 6000 rpm to 8000 rpm.

In still another embodiment of the present disclosure, the process of ultrafiltration in the process for isolation of phycocyanin is carried out using a 10-100 KDa membrane.

In still another embodiment of the present disclosure, the process of stirring/mixing is carried out by a stirrer or a mixer.

In still another embodiment of the present disclosure, the biomass is homogenized by a homogenizer.

In still another embodiment of the present disclosure, the homogenization is carried out under pressure.

In still another embodiment of the present disclosure, the biomass is homogenized by a pressure homogenizer.

In still another embodiment of the present disclosure, the homogenization is carried out under 100-300 bar pressure.

In still another embodiment of the present disclosure, the process of pressure homogenization in the process for extraction and isolation of phycocyanin is carried out by a pressure homogenizer.

In still another embodiment of the present disclosure, the process of filtration in the process for extraction and isolation of phycocyanin is carried out by filter(s).

In still another embodiment of the present disclosure, the salt solution is sodium chloride solution, calcium chloride solution or a combination of sodium chloride solution and calcium chloride solution.

In still another embodiment of the present disclosure, the concentration of the salt solution ranges from about 5% to 10%.

In still another embodiment of the present disclosure, the concentration of the salt solution ranges from 3 to 6%.

In still another embodiment of the present disclosure, the concentration of the salt solution is 8%.

In still another embodiment of the present disclosure, the concentration of the salt solution is 4%.

In a preferred embodiment of the present disclosure, the concentration of the calcium chloride solution is 4%.

In a preferred embodiment of the present disclosure, the concentration of the calcium chloride solution is 8%.

In a preferred embodiment of the present disclosure, the concentration of the sodium chloride solution is 8%.

In still another embodiment of the present disclosure, mixture I comprises salt solution and homogenized biomass.

In still another embodiment of the present disclosure, the concentration of the salt solution in mixture I ranges from 1-4%.

In still another embodiment of the present disclosure, the concentration of the salt solution in mixture I ranges from 2-3%.

In a preferred embodiment of the present disclosure, the concentration of the calcium chloride solution in mixture I ranges from 2-3%.

In another preferred embodiment of the present disclosure, the concentration of the sodium chloride solution in mixture I ranges from 2-3%.

In still another embodiment of the present disclosure, the solvent is selected from a group comprising water, organic solvent, inorganic solvent and combinations thereof.

In still another embodiment of the present disclosure, the acid is selected from a group comprising hydrochloric acid, citric acid, tartaric acid, ascorbic acid and combinations thereof.

In still another embodiment of the present disclosure, the concentration of the acid solution ranges from about 0.5% to 5%.

In a preferred embodiment of the present disclosure, the concentration of the acid solution ranges from 0.75% to 2.5%.

In a more preferred embodiment of the present disclosure, the concentration of the acid solution is 1%.

In still another embodiment of the present disclosure, mixture I comprises salt solution and homogenized biomass.

In still another embodiment of the present disclosure, the pH of the mixture I is adjusted by adding acid.

In still another embodiment of the present disclosure, the pH of the mixture I is adjusted to a range from 4 to 6 by adding acid.

In a preferred embodiment of the present disclosure, the pH of the mixture I is adjusted to 5 by adding acid.

In still another embodiment of the present disclosure, the acid treated mixture comprises acid and the mixture I.

In a preferred embodiment of the present disclosure, the acid treated mixture comprises citric acid and the mixture I.

In still another embodiment of the present disclosure, the filtrate I is a filtrate which is devoid of insoluble solids obtained from the filtration of acid treated mixture.

In a preferred embodiment of the present disclosure, the filtrate I is a filtrate which is devoid of insoluble solids obtained from the filtration of citric acid treated mixture.

In still another embodiment of the present disclosure, the filtration is carried out by filter(s).

In still another embodiment of the present disclosure, the filtrate I is subjected to further ultrafiltration to concentrate the filtrate I to obtain a concentrated liquid.

In still another embodiment of the present disclosure, the concentrated liquid is concentrated form of filtrate I.

In still another embodiment of the present disclosure, the biochemical constituent(s) are selected from a group comprising Phycocyanin, Chlorophyll, Polysaccharides, water soluble proteins and combinations thereof.

In still another embodiment of the present disclosure, the mixer is selected from a group comprising mechanical stirrer, anchor, propeller and combinations thereof.

In still another embodiment of the present disclosure, the filter is a centrifuge or a clarifier.

In still another embodiment of the present disclosure, the micro filtration is carried out using 0.01 to 2.0 micron filters.

The residue part is rich in polysaccharides and water dispersible proteins. The acid hydrolysis of the residue yields water soluble proteins.

In a preferred embodiment of the present disclosure, 20-80 KDa membrane is used for carrying out ultrafiltration.

In still another embodiment of the present disclosure, the solvent is selected from a group comprising water, organic solvents, inorganic solvents or combination thereof.

In still another embodiment of the present disclosure, the sugar is selected from a group comprising trehalose, maltodextrin, ensorbate and combinations thereof.

In yet another embodiment of the present disclosure, the process of stirring/mixing is carried out by a stirrer or a mixer.

In still another embodiment of the present disclosure, the process of filtration in the process for extraction and isolation of magnesium chlorophyll is carried out by filter(s).

In still another embodiment of the present disclosure, the distillation is carried out under vacuum at a temperature ranging from about 60-65° C.

In still another embodiment of the present disclosure, the solvent system used in the process for extraction and isolation of magnesium chlorophyll from wet spirulina biomass selected from a group comprising water, acetone, ethyl acetate or hexane and combinations thereof.

In still another embodiment of the present disclosure, the solvent system used in the process for extraction and isolation of magnesium chlorophyll from wet spirulina biomass comprises ethyl acetate and hexane in the ratio of about 1:1.

In an embodiment of the present disclosure, process for extraction and isolation of magnesium chlorophyll from wet spirulina biomass comprising steps of:
- A. cooling the solution of biomass under stirring conditions;
- B. pressure homogenizing the biomass obtained from previous step to obtain the homogenized biomass;
- C. mixing the salt solution with the homogenized biomass to obtain a mixture I;
- D. adjusting the pH of the mixture I with acid(s) to obtain acid treated mixture;
- E. cooling the acid treated mixture followed by stirring to obtain the cooled acid treated mixture;
- F. separating the insoluble solids from the cooled acid treated mixture to separating the filtrate-I and residue-I;
- G. distilling the residue I obtained from step (F) under vacuum to remove moisture and to obtain residue-II;
- H. mixing the residue-II with organic solvent(s) to obtain mixture VII;
- I. filtering the mixture VII to obtain the residue III and filtrate V;
- J. mixing the residue-III with organic solvent(s) to obtain mixture VIII;
- K. filtering the mixture VIII to obtain the residue IV and filtrate VI;
- L. mixing the residue-IV with organic solvent(s) to obtain mixture IX;
- M. filtering the mixture IX to obtain the residue V and filtrate VII;
- N. combining the filtrate V, filtrate VI and filtrate VII to obtain filtrate VIII; and
- O. distilling the filtrate VIII under vacuum followed by high vacuum distillation to obtain Magnesium chlorophyll.

In another embodiment of the present disclosure, process for extraction and isolation of magnesium chlorophyll from wet spirulina biomass comprising steps of:
- A. cooling the aqueous solution of spirulina biomass to about 15-20° C. under stirring conditions, wherein said aqueous solution of spirulina biomass is prepared by adding spirulina biomass suspended in demineralised water and cooled to about 15-20° C. under stirring conditions;
- B. pressure homogenizing the biomass obtained from previous step at about 100 bar for about 1 hour to obtain homogenized biomass;
- C. mixing calcium chloride solution with the homogenized biomass to obtain a mixture I;
- D. adjusting pH of the mixture I with citric acid to obtain acid treated mixture maintaining the pH ranging from 4 to 6;
- E. cooling the acid treated mixture to about 15-20° C. followed by stirring to obtain the cooled acid treated mixture;
- F. separating the insoluble solids from the cooled acid treated mixture to obtain filtrate-I and residue-I by centrifugation at about 7000 rpm;
- G. distilling the residue-I obtained in step (F) under vacuum at a temperature ranging from about 60-65° C. to remove moisture and to obtain residue-II;
- H. mixing the residue-II with about 8 volumes of solvent mixture and stirring for about 2 hours to obtain mixture-VII, wherein the solvent system comprises ethyl acetate and hexane in the ratio of about 1:1;
- I. filtering the mixture-VII to obtain residue III and filtrate-V;
- J. mixing the residue-III with about 6 volumes of solvent mixture and stirring for about 2 hours to obtain mixture-VIII;
- K. filtering the mixture-VIII to obtain residue-IV and filtrate-VI;
- L. mixing the residue-IV with about 4 volumes of solvent mixture and stirring to obtain mixture-IX, wherein the solvent system comprises ethyl acetate and hexane in the ratio of about 1:1;
- M. filtering the mixture-IX to obtain residue-V and filtrate-VII;
- N. combining the filtrate-V, filtrate-VI and filtrate-VII to obtain filtrate-VIII; and
- O. distilling the filtrate-VIII at about 60-65° C. under vacuum followed by high vacuum distillation to obtain the magnesium chlorophyll.

In an embodiment of the present disclosure, magnesium chlorophyll content of the extract is ranging from about 35% to 45%.

In an embodiment of the present disclosure, yield of magnesium chlorophyll is 1.5% based on the dry spirulina biomass.

The present disclosure furthermore relates to the process for extraction and isolation of hydrolysed protein from the wet algal biomass comprises steps of:
- cooling the aqueous solution of algal biomass;
- pressure homogenizing the wet biomass and extraction of the biomass with salt solution in presence of acidic conditions under cooling conditions to obtain a suspension, followed by centrifuging the suspension to separate filtrate and residue;
- drying the residue, treating the residue with solvent followed by filtration to obtain a filtrate and residue-V, and subjecting the filtrate to distillation to obtain the purified magnesium chlorophyll from the wet algal biomass, wherein the solvent treatment followed by filtration is repeated one or more times to obtain multiple filtrates which is combined when subjecting to the distillation; and
- mixing residue-V obtained after chlorophyll extraction with water and hydrochloric acid, heating the resulting mixture followed by cooling and adjusting the pH to 5.2 using caustic soda solution, filtering the resulting solution, by removing the salt through ultrafiltration, concentrating and spray drying the protein solution to give the hydrolysed protein.

In an embodiment of the present disclosure, the wet algal biomass is blue-green algae, more preferably spirulina.

In another embodiment of the present disclosure, the blue-green algae is spirulina.

In yet another embodiment of the present disclosure, the solid content of wet spirulina biomass is about 14-20%.

In still another embodiment of the present disclosure, the cooling is carried out at a temperature ranging from about 10° C. to about 30° C., preferably 15° C. to about 20° C.

In still another embodiment of the present disclosure, the process for extraction and isolation of magnesium chlorophyll from wet spirulina biomass is carried out at a pH ranging from about 4 to 6 and at a temperature ranging from about 10° C. to 25° C.

In still another embodiment of the present disclosure, the process of centrifugation in the process for extraction and isolation of hydrolysed protein is carried out at a speed of about 6000 rpm to 8000 rpm.

In still another embodiment of the present disclosure, the process of ultrafiltration in the process for extraction and isolation of hydrolysed protein is carried out using a 10-100 KDa membrane.

In still another embodiment of the present disclosure, the process of stirring/mixing is carried out by a stirrer or a mixer.

In still another embodiment of the present disclosure, the biomass is homogenized by a homogenizer.

In still another embodiment of the present disclosure, the homogenization is carried out under pressure.

In still another embodiment of the present disclosure, the biomass is homogenized by a pressure homogenizer.

In still another embodiment of the present disclosure, the homogenization is carried out under 100-300 bar pressure.

In still another embodiment of the present disclosure, the process of pressure homogenization in the process for extraction of hydrolysed protein is carried out by a pressure homogenizer.

In still another embodiment of the present disclosure, the process of filtration in the process for extraction and isolation of hydrolysed protein is carried out by filter(s).

In still another embodiment of the present disclosure, the salt solution is sodium chloride solution, calcium chloride solution or a combination of sodium chloride solution and calcium chloride solution.

In still another embodiment of the present disclosure, the concentration of the salt solution ranges from about 5% to 10%.

In still another embodiment of the present disclosure, the concentration of the salt solution ranges from 3 to 6%.

In still another embodiment of the present disclosure, the concentration of the salt solution is 8%.

In still another embodiment of the present disclosure, the concentration of the salt solution is 4%.

In a preferred embodiment of the present disclosure, the concentration of the calcium chloride solution is 4%.

In a preferred embodiment of the present disclosure, the concentration of the calcium chloride solution is 8%.

In a preferred embodiment of the present disclosure, the concentration of the sodium chloride solution is 8%.

In still another embodiment of the present disclosure, the mixture I comprises salt solution and homogenized biomass.

In still another embodiment of the present disclosure, the concentration of the salt solution in mixture I ranges from 1-4%.

In still another embodiment of the present disclosure, the concentration of the salt solution in mixture I ranges from 2-3%.

In a preferred embodiment of the present disclosure, the concentration of the calcium chloride solution in mixture I ranges from 2-3%.

In another preferred embodiment of the present disclosure, the concentration of the sodium chloride solution in mixture I ranges from 2-3%.

In still another embodiment of the present disclosure, the solvent is selected from a group comprising water, organic solvent, inorganic solvent and combinations thereof.

In still another embodiment of the present disclosure, the acid is selected from a group comprising hydrochloric acid, citric acid, tartaric acid, ascorbic acid and combinations thereof.

In still another embodiment of the present disclosure, the concentration of the acid solution ranges from about 0.5% to 5%.

In a preferred embodiment of the present disclosure, the concentration of the acid solution ranges from 0.75% to 2.5%.

In a more preferred embodiment of the present disclosure, the concentration of the acid solution is 1%.

In still another embodiment of the present disclosure, the mixture I comprises salt solution and homogenized biomass.

In still another embodiment of the present disclosure, the pH of the mixture I is adjusted by adding acid.

In still another embodiment of the present disclosure, the pH of the mixture I is adjusted to a range from 4 to 6 by adding acid.

In a preferred embodiment of the present disclosure, the pH of the mixture I is adjusted to 5 by adding acid.

In still another embodiment of the present disclosure, the acid treated mixture comprises acid and the mixture I.

In a preferred embodiment of the present disclosure, the acid treated mixture comprises citric acid and the mixture I.

In still another embodiment of the present disclosure, the filtrate I is a filtrate which is devoid of insoluble solids obtained from the filtration of acid treated mixture.

In a preferred embodiment of the present disclosure, the filtrate I is a filtrate which is devoid of insoluble solids obtained from the filtration of citric acid treated mixture.

In still another embodiment of the present disclosure, the filtration is carried out by filter(s).

In still another embodiment of the present disclosure, filtrate I is subjected to further ultrafiltration to concentrate the filtrate I to obtain a concentrated liquid.

In still another embodiment of the present disclosure, the concentrated liquid is concentrated form of filtrate I.

In still another embodiment of the present disclosure, the biochemical constituent(s) are selected from a group comprising Phycocyanin, Chlorophyll, Polysaccharides, water soluble proteins and combinations thereof.

In still another embodiment of the present disclosure, the mixer is selected from a group comprising mechanical stirrer, anchor, propeller and combinations thereof.

In still another embodiment of the present disclosure, the filter is a centrifuge or a clarifier.

In still another embodiment of the present disclosure, the fine microfiltration is carried out using 0.01 to 2.0 micron filters.

In still another embodiment of the present disclosure, the suitable filtration is ultrafiltration or microfiltration.

The residue part is rich in polysaccharides and water dispersible proteins. The acid hydrolysis of the residue yields water soluble proteins.

In a preferred embodiment of the present disclosure, 20-80 KDa membrane is used for carrying out ultrafiltration.

In still another embodiment of the present disclosure, the solvent is selected from a group comprising water, organic solvents, inorganic solvents or combination thereof.

In still another embodiment of the present disclosure, the sugar is selected from a group comprising trehalose, maltodextrin, ensorbate and combinations thereof.

In yet another embodiment of the present disclosure, the process of stirring/mixing is carried out by a stirrer or a mixer.

In still another embodiment of the present disclosure, the process of filtration in the process for extraction and isolation of hydrolysed protein is carried out by filter(s).

In still another embodiment of the present disclosure, the distillation is carried out under vacuum at a temperature ranging from about 60-65° C.

In still another embodiment of the present disclosure, the solvent system used in the process for isolation of hydrolysed protein is carried out by a selected from a group comprising water, acetone, ethyl acetate or hexane and combinations thereof.

In still another embodiment of the present disclosure, the solvent system used in the process for extraction and isolation of hydrolysed protein comprises ethyl acetate and hexane in the ratio of about 1:1.

In an embodiment of the present disclosure, the process for extraction and isolation of hydrolysed protein from spirulina biomass comprising steps of:
a. cooling the aqueous solution of spirulina biomass to about 15-20° C. under stirring conditions, wherein said aqueous solution of spirulina biomass is prepared by adding spirulina biomass suspended in demineralised water and cooled to about 15-20° C. under stirring conditions;
b. pressure homogenizing the biomass obtained from previous step at about 100 bar for about 1 hour to obtain homogenized biomass;
c. mixing calcium chloride solution with the homogenized biomass to obtain a mixture I;
d. adjusting pH of the mixture I with citric acid to obtain acid treated mixture maintaining the pH ranging from 4 to 6;
e. cooling the acid treated mixture to about 15-20° C. followed by stirring to obtain the cooled acid treated mixture;
f. separating the insoluble solids from the cooled acid treated mixture to obtain filtrate-I and residue-I by centrifugation at about 7000 rpm;
g. distilling the residue-I obtained in step (f) under vacuum at a temperature ranging from about 60-65° C. to remove moisture and to obtain residue-II;
h. mixing the residue-II with organic solvent(s) to obtain mixture VII;
i. filtering the mixture VII to obtain the residue III and filtrate V;
j. mixing the residue-III with organic solvent(s) to obtain mixture VIII;
k. filtering the mixture VIII to obtain the residue IV and filtrate VI;
l. mixing the residue-IV with organic solvent(s) to obtain mixture IX;
m. filtering the mixture IX to obtain the residue V and filtrate VII;
n. combining the filtrate V, filtrate VI and filtrate VII to obtain filtrate VIII;
o. distilling the filtrate VIII under vacuum followed by high vacuum distillation to obtain Magnesium chlorophyll;
p. mixing residue-V obtained after chlorophyll extraction with water and hydrochloric acid to obtain a residual mixture;
q. heating the residual mixture followed by cooling and adjusting the pH to 5.2 using caustic soda solution to obtain slightly acidic residual mixture;
r. filtering the slightly acidic residual mixture to obtain slightly acidic filtrate and to remove the solids followed by ultrafiltration to remove salts; and
s. concentrating and spray drying the slightly acidic filtrate to give the hydrolysed protein.

In another embodiment of the present disclosure, the yield of hydrolysed protein of spirulina biomass is ranging from about 10% to 15%.

In yet another embodiment of the present disclosure, the protein content of hydrolysed protein of spirulina biomass is ranging from about 60% to 70%.

EXAMPLES

Additional embodiments and features of the present disclosure will be apparent to one of ordinary skill in the art based upon description and examples provided herein. However, the examples below should not be construed to limit the scope of the present disclosure.

Example 1: Procedure for Extracting Phycocyanin

Experiment 1

The spirulina biomass 2000 gms (solid content 15.2% and phycocyanin content 18%) suspended in 2000 ml of demineralised water and cooled to 15-20° C. under stirring using a mechanical stirrer. The homogenized biomass was pressure homogenized for one hour at 100 bar. The resultant mass was mixed with a solution of calcium chloride (170 gm $CaCl_2$ in 4000 ml of demineralized water) and the pH of the mixture was adjusted to 5.0 by 1% citric acid solution. The total mass was cooled to 15-20° C. and stirred with a mechanical stirrer for 2 hours. The mass was then centrifuged at 7000 rpm and the filtrate was collected.

Results: Volume=7500 ml, Concentration=3%, Colour value at 620 nm=50, Crude phycocyanin=18%, Residue=1200 gms.

Experiment 2

The spirulina water extract 7500 ml from the experiment 1 was subjected to ultrafiltration through a 30-50 KDa membrane and the concentrated solution was mixed with 5000 ml demineralised water. The solution was subjected to ultrafiltration till the concentration reaches to 2%. The solution was mixed with 30 gms of Celite HYFLO SUPER-CEL, stirred for one hour and centrifuged at 6000 rpm. The filtrated was collected and cooled to 15-20 C.

Results: Volume=4000 ml, Concentration=1.5%, Colour value=310 units.

Experiment 3

The water extract 4000 ml from experiment 2 was mixed with 8000 ml of demineralised water and filtered through 0.1 micron filter at less than I bar pressure. The filtrate was further concentrated through ultrafiltration. The concentrated mass was further diluted with 4000 ml demineralised water and concentrated using ultrafiltration to 8-10%.

Results: Volume=500 ml, concentration=8%, colour value=520.

Experiment 4

The 500 ml of the concentrated phycocyanin solution was mixed with 25 gm trehalose and the resultant solution was filtered through a sparkler filter and spray dried.

Results: Weight=50 gms, colour value=195, moisture=4%, phycocyanin=24%.

Experiment 5

The phycocyanin blue 50 gms from the above experiment was heated to 80-85° C. in an oven for 8 hours and cooled to 25° C. and vacuum packed.

Results: Weight=48 gms, colour value=190, moisture=2% phycocyanin=23.5%

Example 2: Procedure for Extracting Phycocyanin

Experiment 6

The spirulina biomass 1000 gms (solid content 16% and phycocyanin content 17%) suspended in 1500 ml of demineralised water and cooled to 15-20° C. under stirring using a mechanical stirrer. The resultant biomass was pressure homogenized for one hour at 120 bar. The homogenized mass was mixed with a solution of calcium chloride (90 gm $CaCl_2$ in 2000 ml of demineralized water) and the pH of the mixture was adjusted to 4.8 by 1% citric acid solution. The total mass was cooled to 15-20° C. and stirred with a mechanical stirrer for 2 hours. The mass was then centrifuged at 7500 rpm and the filtrate was collected.

Results: Volume=4000 ml, Concentration=4%, Colour value at 620 nm=45, Crude phycocyanin=16%, Residue=700 gms.

Experiment 7

The spirulina water extract 4000 ml from the experiment 6 was subjected to ultrafiltration through a 30-50 KDa membrane and the concentrated solution was mixed with 2000 ml demineralised water. The solution was subjected to ultrafiltration till the concentration reaches to 2%. The solution was mixed with 15 gms of Celite HYFLO SUPER-CEL, stirred for one hour and centrifuged at 6500 rpm. The filtrated was collected and cooled to 15-20 C.

Results: Volume=1500 ml, Concentration=1.6%, Colour value=320 units.

Experiment 8

The water extract 1500 ml from experiment 7 was mixed with 3000 ml of demineralised water and filtered through 0.1 micron filter at less than I bar pressure. The filtrate was further concentrated through ultrafiltration. The concentrated mass was further diluted with 1500 ml demineralised water and concentrated using ultrafiltration to 8-10%.

Results: Volume=300 ml, concentration=7.5%, colour value=515.

Experiment 9

The 300 ml of the concentrated phycocyanin solution was mixed with 12 gm maltodextrin and the resultant solution was filtered through a filter and spray dried.

Results: Weight=23 gms, colour value=196, moisture=3.5%, phycocyanin=24.5%.

Experiment 10

The phycocyanin blue 20 gms from the above experiment was heated to 80-85° C. in an oven for 8 hours and cooled to 25 C and vacuum packed.

Results: Weight=20 gms, colour value=186, moisture=2.6% phycocyanin=24%.

Example 3: Procedure for Extracting Magnesium Chlorophyll

Experiment 11

The residue 1200 gms (expt. No. 1) after water extraction of spirulina was distilled at 60-65° C. under vacuum to remove 50% of moisture. The residue 600 gms mixed with 8 volumes of solvent mixture (Ethyl acetate and Hexanes in the ratio 1:1) and stirred for 2 hours and the mixture was filtered. The residue is again treated with 6 volumes solvent mixture and stirred for 2 hours and filtered. The residue (polysaccharides) again mixed with 4 volumes of solvent mixture and stirred and filtered. The combined filtrate was concentrated by distilling at 60-65° C. under vacuum and the solid obtained was subjected distillation at high vacuum of 5-10 mm of mercury to get the Mg Chlorophyll.

Results: Mg chlorophyll=16 gm, Chlorophyll content=38%, Moisture=3.5%, Residue=160 gm, protein content=68%.

Experiment 12

The residue (polysaccharides) 700 gms (expt no. 6) was distilled under vacuum to remove 55% of water at 60-65 C. The residue 315 gms was mixed with solvent mixture (Ethyl acetate and Hexanes in the ratio 1:1) and stirred for 2 hours and the mixture was filtered. The residue is again treated with 6 volumes solvent mixture and stirred for 2 hours and filtered. The residue again mixed with 4 volumes of solvent mixture and stirred and filtered. The combined filtrate was concentrated by distilling at 60-65 C under vacuum and the solid obtained was subjected to distillation under high vacuum of 5-10 mm of Hg to get the Mg Chlorophyll.

Results: The Mg chlorophyll=9 gm, Chlorophyll content=36%, Moisture=3.2%, Residue=75 gm, protein content=67%.

Example 4: Procedure for Extracting Hydrolysed Protein

Experiment 13

The Spirulina residue 100 gms [obtained from experiment 11] after chlorophyll extraction was mixed with 400 ml water and 100 ml hydrochloric acid (35%) and heated at 60-65° C. for 6 hours. The reaction mixture was then cooled to 25-30° C. and the pH was adjusted to 5.2 using 20% caustic soda solution (150 ml). It was then filtered and the filtrate was subjected to membrane filtration to remove the salt. The protein solution was then concentrated and spray dried to give the hydrolysed protein.

Results: Protein=67 gm, NaCl=6%; Moisture=4.5%, Protein content=65%

Experiment 14

The Spirulina residue 70 gms (experiment 12) after chlorophyll extraction was mixed with 280 ml water and 70 ml hydrochloric acid (35%) and heated at 60-65° C. for 6 hours. The reaction mixture was then cooled to 25-30° C. and the pH was adjusted to 5.2 using 20% caustic soda solution (110 ml). It was then filtered and the filtrate was subjected to membrane filtration to remove the salt. The protein solution was then concentrated and spray dried to give the hydrolysed protein.

Results: Protein=48 gm, NaCl=5%; Moisture=3%, Protein content=70%

Comparative Studies

Example 5

Experiment 15—Low Temperature Change Resulted in Low Yield

Stage 1: The spirulina biomass 2000 gms (solid content 15.2% and phycocyanin 18%) suspended in 2000 mL demineralized water and cooled to 10° C. using a mechanical stirrer. The resultant biomass was pressure homogenized for one hour at 100 bar. The homogenized mass was mixed with a solution of calcium chloride (170 gm $CaCl_2$ in 4000 mL of demineralized water) and the pH was adjusted to 4.8 by 1% citric acid solution. The total mass was cooled to 10° C. and stirred with a mechanical stirrer for 2 hours. The mass was centrifuged at 7500 rpm and the filtrate was collected.

Results: Volume=7450 ml, Concentration=2.9%, Color value at 620 nm=35 units, Crude phycocyanin=15.9%, Residue=1700 gms Stage 2: The spirulina water extract 7450 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and centrifuged at 6000 rpm. The filtrate was collected and cooled to 10° C.

Results: Volume=4000 ml, Concentration=1.1%, Color value at 620 nm=270 units

Stage 3: The water extract 4000 ml from the above experiment was mixed with 8000 ml of demineralized water and filtered through 0.1-micron filter at less than 1 bar pressure. The filtrate was further concentrated through ultrafiltration. The concentrated mass was further diluted with 4000 ml demineralized water and concentrated using ultrafiltration to 8-10%.

Results: Volume=255 ml, Concentration=7.2%, Color value at 620 nm=460 units.

Stage 4: The 255 ml of concentrated phycocyanin solution was mixed with 25.5 gms of trehalose and the resultant solution was filtered through a sparkle filter and spray dried.

Results: Weight=40 gms, Color value=188 units, moisture=4.3%, phycocyanin=23.8%.

Stage 5: The phycocyanin blue 40 gms from the above experiment was heated to 80-85° C. in an oven for 8 hours and cooled to 25° C. and vacuum packed.

Results: Weight=38 gms, Color value=184 units, moisture=2.2%, phycocyanin=23.4%, Inference: The process disclosed in Example 1 of the present application for extracting phycocyanin results the yield of product 15.78 wt % (phycocyanin weight 48 gms) whereas the process described in Example 6 of the present application for extracting phycocyanin results the yield of product 12.5 wt % (phycocyanin weight 38 gms). Thus, these studies signify that maintaining the temperature ranging from about 15-20° C. is important to obtain high yield of purified product phycocyanin.

Example 6

Experiment 16—Low Pressure Resulted in Low Yield

Stage 1: The spirulina biomass 2000 gms (solid content 15.2% and phycocyanin 18%) suspended in 2000 mL demineralized water and cooled to 15-20° C. using a mechanical stirrer. The resultant biomass was pressure homogenized for one hour at 50 bar. The homogenized mass was mixed with a solution of calcium chloride (170 gm $CaCl_2$ in 4000 mL of demineralized water) and the pH was adjusted to 4.8 by 1% citric acid solution. The total mass was cooled to 15-20° C. and stirred with a mechanical stirrer for 2 hours. The mass was centrifuged at 7500 rpm and the filtrate was collected.

Results: Volume=7400 ml, Concentration=3.2%, Color value at 620 nm=40 units, Crude phycocyanin=16.9%, Residue=1600 gms.

Stage 2: The spirulina water extract 7400 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and centrifuged at 6000 rpm. The filtrate was collected and cooled to 15-20° C.

Results: Volume=4000 ml, Concentration=1.1%, Color value at 620 nm=240 units

Stage 3: The water extract 4000 ml from the above experiment was mixed with 8000 ml of demineralized water and filtered through 0.1 micron filter at less than 1 bar pressure. The filtrate was further concentrated through ultrafiltration. The concentrated mass was further diluted with 4000 ml demineralized water and concentrated using ultrafiltration to 8-10%.

Results: Volume=280 ml, Concentration=6%, Color value at 620 nm=450 units

Stage 4: The 280 ml of concentrated phycocyanin solution was mixed with 22 gms of trehalose and the resultant solution was filtered through a sparkle filter and spray dried.

Results: Weight=35 gms, Color value=189 units, moisture=4.1%, phycocyanin=23.8%, Stage 5: The phycocyanin blue 35 gms from the above experiment was heated to 80-85° C. in an oven for 8 hours and cooled to 25° C. and vacuum packed.

Results: Weight=33 gms, Color value=184, moisture=2.3%, phycocyanin=23%.

Inference: The process disclosed in Example 1 of the present application for extracting phycocyanin results the yield of product 15.78 (phycocyanin weight 48 gms) whereas the process described in Example 7 of the present application for extracting phycocyanin results the yield of product 10.85 (phycocyanin weight 33 gms). Thus, these studies signify that maintaining the optimal pressure of ranging from about 100 bar to 120 bar is important to obtain high yield of purified product phycocyanin.

Example 7

Experiment 17—High Pressure Yielded Low Yield

Stage 1: The spirulina biomass 2000 gms (solid content 15.2% and phycocyanin 18%) suspended in 2000 mL demineralized water and cooled to 15-20° C. using a mechanical stirrer. The resultant biomass was pressure homogenized for one hour at 150 bar. The homogenized mass was mixed with a solution of calcium chloride (170 gm CaCl2 in 2000 mL of demineralized water) and the pH was adjusted to 4.8 by 1% citric acid solution. The total mass was cooled to 15-20° C. and stirred with a mechanical stirrer for 2 hours. The mass was centrifuged at 7500 rpm and the filtrate was collected.

Results: Volume=7600 ml, Concentration=2.9%, Color value at 620 nm=42 units, Crude phycocyanin=17%, Residue=1600 gms.

Stage 2: The spirulina water extract 7600 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and Results: Volume centrifuged at 6000 rpm. The filtrate was collected and cooled to 15-20° C.=4000 ml, Concentration=1.2%, Color value at 620 nm=255 units Stage 3: The water extract 4000 ml from the above experiment was mixed with 8000 ml of demineralized water and filtered through 0.1 micron filter at less than 1 bar pressure. The filtrate was further concentrated through ultrafiltration. The concentrated mass was further diluted with 5000 ml demineralized water and concentrated using ultrafiltration to 8-10%.

Results: Volume=290 ml, Concentration=6.2%, Color value at 620 nm=440 units

Stage 4: The 290 ml of concentrated phycocyanin solution was mixed with 24 gms of trehalose and the resultant solution was filtered through a sparkle filter and spray dried.

Results: Weight=37 gms, Color value=188 units, moisture=4.3%, phycocyanin=23.5%.

Stage 5: The phycocyanin blue 37 gms from the above experiment was heated to 80-85° C. in an oven for 8 hours and cooled to 25° C. and vacuum packed.

Results: Weight=36 gms, Color value=183, moisture=2.4%, phycocyanin=23.2%.

Inference: The process disclosed in Example 1 of the present application for extracting phycocyanin results the yield of product 15.78 wt % (phycocyanin weight 48 gms) whereas the process described in Example 8 of the present application for extracting phycocyanin results the yield of product 11.84 wt % (phycocyanin weight 36 gms). Thus, these studies signify that maintaining the optimal pressure of ranging from about 100 bar to 120 bar is important to obtain high yield of purified product phycocyanin.

Example 8

Experiment 18—Less CaCl$_2$ Resulted in Low Yield

Stage 1

The spirulina biomass 2000 gms (solid content 15.2% and phycocyanin 18%) suspended in 2000 mL demineralized water and cooled to 15-20° C. using a mechanical stirrer. The resultant biomass was pressure homogenized for one hour at 100 bar. The homogenized mass was mixed with a solution of calcium chloride (136 gms CaCl$_2$ in 4000 mL of demineralized water) and the pH was adjusted to 4.8 by 1% citric acid solution. The total mass was cooled to 15-20° C. and stirred with a mechanical stirrer for 2 hours. The mass was centrifuged at 7500 rpm and the filtrate was collected.

Results: Volume=7300 ml, Concentration=2.8%, Color value at 620 nm=37 units, Crude phycocyanin=17.4%, Residue=1650 gms.

Stage 2: The spirulina water extract 7300 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and centrifuged at 6000 rpm. The filtrate was collected and cooled to 15-20° C.

Results: Volume=4000 ml, Concentration=1.2%, Color value at 620 nm=255 units.

Stage 3: The water extract 4000 ml from the above experiment was mixed with 8000 ml of demineralized water and filtered through 0.1 micron filter at less than 1 bar pressure. The filtrate was further concentrated through ultrafiltration. The concentrated mass was further diluted with 5000 ml demineralized water and concentrated using ultrafiltration to 8-10%.

Results: Volume=240 ml, Concentration=7.4%, Color value at 620 nm=455 units.

Stage 4: The 240 ml of concentrated phycocyanin solution was mixed with 24.5 gms of trehalose and the resultant solution was filtered through a sparkle filter and spray dried.

Results: Weight=36 gms, Color value=184, moisture=4.4%, phycocyanin=23.5%.

Stage 5: The phycocyanin blue 36 gms from the above experiment was heated to 80-85° C. in an oven for 8 hours and cooled to 25° C. and vacuum packed.

Results: Weight=34.5 gms, Color value=184 units, moisture=2.6%, phycocyanin=23.2%.

Inference: The process disclosed in Example 1 of the present application for extracting phycocyanin results the yield of product 15.78 wt % (phycocyanin weight 48 gms) whereas the process described in Example 9 of the present application for extracting phycocyanin results the yield of product 11.34 wt % (phycocyanin weight 34.5 gms). Thus, these studies signify that maintaining the optimal CaCl$_2$ content (4 to 4.5 CaCl$_2$ content) is important to obtain high yield of purified product phycocyanin.

Example 9

Experiment 19—Low pH Resulted in Low Yield

Stage 1: The spirulina biomass 2000 gms (solid content 15.2% and phycocyanin 18%) suspended in 2000 mL demineralized water and cooled to 15-20° C. using a mechanical stirrer. The resultant biomass was pressure homogenized for one hour at 100 bar. The homogenized mass was mixed with a solution of calcium chloride (170 gm CaCl2 in 4000 mL of demineralized water) and the pH was adjusted to 3.0 by 1% citric acid solution. The total mass was cooled to 15-20° C. and stirred with a mechanical stirrer for 2 hours. The mass was centrifuged at 7500 rpm and the filtrate was collected.

Results: Volume=7400 ml, Concentration=3.1%, Color value at 620 nm=35 units, Crude phycocyanin=16%, Residue=1550 gms.

Stag 2: The spirulina water extract 7400 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and centrifuged at 6000 rpm. The filtrate was collected and cooled to 15-20° C.

Results: Volume=4000 ml, Concentration=1.4%, Color value at 620 nm=250 units

Stage 3: The water extract 4000 ml from the above experiment was mixed with 8000 ml of demineralized water and filtered through 0.1 micron filter at less than 1 bar pressure. The filtrate was further concentrated through ultrafiltration. The concentrated mass was further diluted with 5000 ml demineralized water and concentrated using ultrafiltration to 8-10%.

Results: Volume=300 ml, Concentration=7.9%, Color value at 620 nm=330 units

Stage 4: The 300 ml of concentrated phycocyanin solution was mixed with 20 gms of trehalose and the resultant solution was filtered through a sparkle filter and spray dried.

Results: Weight=40 gms, Color value=190.5 units, moisture=3.9%, phycocyanin=23.5%.

Stage 5: The phycocyanin blue 40 gms from the above experiment was heated to 80-85° C. in an oven for 8 hours and cooled to 25° C. and vacuum packed.

Results: Weight=38 gms, Color value=185 units, moisture=2.2%, phycocyanin=23%.

Inference: The process disclosed in Example 1 of the present application for extracting phycocyanin results the yield of product 15.78 wt % (phycocyanin weight 48 gms) whereas the process described in Example 11 of the present application for extracting phycocyanin results the yield of product 12.5 wt % (phycocyanin weight 38 gms). Thus, these studies signify that maintaining the optimal pH [4 to 5 pH] content is important to obtain high yield of purified product phycocyanin.

Example 10

Experiment 20—Spirulina Powder Resulted in Lower Yield

Stage 1: The spirulina powder 300 gms (phycocyanin 12%) suspended in 2000 mL demineralized water and cooled to 15-20° C. using a mechanical stirrer. The resultant biomass was pressure homogenized for one hour at 100 bar. The homogenized mass was mixed with a solution of calcium chloride (170 gm CaCl2 in 4000 mL of demineralized water) and the pH was adjusted to 4.8 by 1% citric acid solution. The total mass was cooled to 15-20° C. and stirred with a mechanical stirrer for 2 hours. The mass was centrifuged at 7500 rpm and the filtrate was collected.

Results: Volume=6000 ml, Concentration=2.9%, Color value at 620 nm=40 units, Crude phycocyanin=14%, Residue=1500 gms Stage 2: The spirulina water extract 6000 ml from the above experiment was subjected to ultrafiltration through a 30-50 KDa membrane and the concentrated solution was mixed with 5000 ml demineralized water. The solution was subjected to ultrafiltration till the concentration reaches 2%. The solution was mixed with 30 gms of celite HYFLO SUPER-CEL, stirred for one hour and centrifuged at 6000 rpm. The filtrate was collected and cooled to 15-20° C.

Results: Volume=3500 ml, Concentration=1.2%, Color value at 620 nm=250 units

Stage 3: The water extract 3500 ml from the above experiment was mixed with 8000 ml of demineralized water and filtered through 0.1 micron filter at less than 1 bar pressure. The filtrate was further concentrated through ultrafiltration. The concentrated mass was further diluted with 5000 ml demineralized water and concentrated using ultrafiltration to 8-10%.

Results: Volume=325 ml, Concentration=7.0%, Color value at 620 nm=350 units

Stage 4: The 325 ml of concentrated phycocyanin solution was mixed with 20 gms of trehalose and the resultant solution was filtered through a sparkle filter and spray dried.

Results: Weight=37 gms, Color value=190 units, moisture=3.9%, phycocyanin=24.1%

Stage 5: The phycocyanin blue 37 gms from the above experiment was heated to 80-85° C. in an oven for 8 hours and cooled to 25° C. and vacuum packed.

Results: Weight=36 gms, Color value=186 units, moisture=2.1%, phycocyanin=23.8%.

Inference: The process disclosed in Example 1 of the present application for extracting phycocyanin results the yield of product 15.78 wt % (phycocyanin weight 48 gms) whereas the process described in Example 13 of the present application for extracting phycocyanin results the yield of product 11.84 wt % (phycocyanin weight 36 gms). Thus, these studies signify that the process requires fresh spirulina biomass to obtain high yield of purified product phycocyanin than powdered form of Spirulina biomass.

We claim:

1. A process for extraction and isolation of a biochemical constituent from wet biomass comprising steps of:
   pressure homogenizing the wet biomass followed by extraction of the wet biomass with salt solution in the presence of acid under a cooling condition followed by centrifuging the wet biomass to separate a first filtrate and a first residue from the wet biomass;
   and one of the following steps (i) or (ii):
   (i) concentrating the first filtrate followed by washing with solvent to remove impurities and to obtain a purified biochemical constituent comprising phycocyanin from the first filtrate;
   or
   (ii) drying the residue, treating the first residue with solvent followed by filtration to obtain a second filtrate and a second residue, and subjecting the second filtrate to distillation to obtain a purified biochemical constituent Magnesium Chlorophyll from the wet biomass, wherein the treating with the solvent followed by the filtration is repeated one or more times to obtain multiple, additional second filtrates which are combined and subjected to distillation.

2. The process as claimed in claim 1, wherein the biomass is spirulina.

3. The process as claimed in claim 1, wherein the process comprises performing step (i).

4. The process as claimed in claim 1, wherein the process comprises performing step (ii).

5. The process as claimed in claim 1, wherein solid content of wet biomass is 14-20%.

6. The process as claimed in claim 1, wherein the process is steps of pressure homogenizing and extraction of the wet biomass are carried out at a pH range of about 3 to 6 and at a temperature range of about 10° C. to 25° C.; the centrifugation is carried out at a speed of 6000 to 8000 rpm; and step (ii) is performed wherein the filtration is carried out by ultrafiltration using a 10-100 KDa membrane or by microfiltration using 0.01 to 2.0 micron filters.

7. The process as claimed in claim 1, wherein the salt solution is sodium chloride solution, calcium chloride solution or a combination of sodium chloride solution and calcium chloride solution;
   wherein the solvent in the salt solution is selected from a group comprising water, an organic solvent, an inorganic solvent or a combination thereof;

wherein concentration of the salt solution ranges from 5% to 10%; and wherein the acid is selected from a group comprising citric acid, tartaric acid, ascorbic acid or combinations thereof, and concentration of the acid ranges from 0.5% to 5%.

8. The process as claimed in claim 1, wherein step (i) is performed and further comprising spray drying the obtained phycocyanin to obtain a dried phycocyanin extract, and wherein crude phycocyanin content of the wet biomass before spray drying is 40-50%, colour value of the dried phycocyanin extract is 180-200, and pure phycocyanin content of the wet biomass is 20-25%.

9. The process as claimed in claim 1, wherein the magnesium chlorophyll content of the wet biomass is within a range of about 35% to 45%.

10. A process for extraction and isolation of a biochemical constituent from wet biomass comprising steps of:

pressure homogenizing the wet biomass followed by extraction of the wet biomass with salt solution in the presence of acid under a cooling condition followed by centrifuging the wet biomass to separate a first filtrate and a residue from the wet biomass;

and one of the following steps (i) or (ii):

(i) concentrating the first filtrate followed by washing with solvent to remove impurities and to obtain a purified biochemical constituent comprising phycocyanin from the first filtrate;

or (ii) drying the residue, treating the first residue with solvent followed by filtration to obtain a second filtrate and a second residue, and subjecting the second filtrate to distillation to obtain a purified biochemical constituent Magnesium Chlorophyll from the wet biomass, wherein the treating with the solvent followed by the filtration is repeated one or more times to obtain multiple, additional second filtrates which are combined and subjected to distillation; and mixing the second residue with water and hydrochloric acid to generate a mixture, heating the mixture followed by cooling and adjusting the pH of the mixture to 5.2 using caustic soda solution to form a resulting solution, filtering the resulting solution to obtain a third filtrate followed by removing salt from the resulting solution through ultrafiltration, and concentrating and spray drying the ultrafiltered resulting solution to obtain a biochemical constituent comprising hydrolysed protein.

11. The process as claimed in claim 10, wherein the biomass is spirulina.

12. The process as claimed in claim 10, wherein the process comprises performing step (ii).

13. The process as claimed in claim 10, wherein solid content of wet biomass is 14-20%.

14. The process as claimed in claim 10, wherein the process is steps of pressure homogenizing and extraction of the wet biomass are carried out at a pH range of about 3 to 6 and at a temperature range of about 10° C. to 25° C.; the centrifugation is carried out at a speed of 6000 to 8000 rpm; and step (ii) is performed wherein the filtration is carried out by ultrafiltration using a 10-100 KDa membrane or by microfiltration using 0.01 to 2.0 micron filters.

15. The process as claimed in claim 10, wherein the salt solution is sodium chloride solution, calcium chloride solution or a combination of sodium chloride solution and calcium chloride solution;

wherein the solvent in the salt solution is selected from a group comprising water, an organic solvent, an inorganic solvent or a combination thereof;

wherein concentration of the salt solution ranges from 5% to 10%; and wherein the acid is selected from a group comprising citric acid, tartaric acid, ascorbic acid or combinations thereof, and concentration of the acid ranges from 0.5% to 5%.

16. The process as claimed in claim 10, wherein step (ii) is performed and wherein protein content of the obtained hydrolysed protein is within a range of about 60% to 70%.

* * * * *